(12) United States Patent
Dunn et al.

(10) Patent No.: US 8,309,755 B2
(45) Date of Patent: *Nov. 13, 2012

(54) MANUFACTURE OF ESTERS

(75) Inventors: John Colin Dunn, Holmfirth (GB); Dinesh Mistry, Bradford (GB); Martin Gower, Halifax (GB); Roger Prétôt, Basel (CH); Markus Schmid, Münchenstein (CH)

(73) Assignee: BASF SE, Ludwigshafen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/092,784

(22) Filed: Apr. 22, 2011

(65) Prior Publication Data
US 2011/0201839 A1    Aug. 18, 2011

(30) Foreign Application Priority Data
Nov. 16, 2005 (GB) ................................. 0523340.8

(51) Int. Cl.
*C07C 67/02* (2006.01)
(52) U.S. Cl. ......................... 560/217; 560/234
(58) Field of Classification Search .................. None
See application file for complete search history.

(56) References Cited

U.S. PATENT DOCUMENTS

| | | | |
|---|---|---|---|
| 3,784,566 A | | 1/1974 | Patterson |
| 3,887,609 A | * | 6/1975 | Strehlke et al. ............... 560/217 |
| 4,543,422 A | | 9/1985 | Farrar |
| 4,748,087 A | | 5/1988 | Davidson et al. |
| 4,898,969 A | | 2/1990 | Jones et al. |
| 5,763,644 A | | 6/1998 | Salek et al. |
| 6,093,842 A | | 7/2000 | Oyevaar et al. |
| 6,417,392 B1 | * | 7/2002 | Nagano et al. ................ 560/222 |

(Continued)

FOREIGN PATENT DOCUMENTS

EP    0090308    10/1983

(Continued)

OTHER PUBLICATIONS

Distillation, Azeotropic, and Extractive in Kirk-Othmer Encyclopedia of Chemical Technology, Michael F. Doherty and Jeffrey P. Knapp, Published Online: Aug. 2, 2004, Copyright © 2001 by John Wiley & Sons, Inc.*

(Continued)

*Primary Examiner* — Karl J Puttlitz
(74) *Attorney, Agent, or Firm* — Shruti Costales

(57) ABSTRACT

The invention relates to a process in which a compound $R_1COOR_3$ (I) is made by a transesterification reaction of an ester compound $R_1COOR_2$ (II) with an alcohol $R_3OH$ (III) in the presence of a transesterification catalyst, wherein $R_1$ is H or $C_{1-4}$ alkyl or $CH_2\!=\!CR_4\!-\!\!$; $R_2$ is $C_{1-4}$ alkyl; $R_3$ is selected from the group consisting of alkyl having at least 4 carbon atoms, cycloalkyl having at least 5 carbon atoms, aryl, aralkyl, alkaryl and amino alkyl; and $R_4$ is —H or —$C_{1-4}$ alkyl, wherein alcohol $R_2OH$ (IV) is formed as a byproduct and in which said byproduct (IV) is removed by distillation in the presence of an entrainer, in which the entrainer is a compound that suppresses the formation of an azeotrope between compound (II) and byproduct (IV). The process can be useful in the preparation of esters such as dimethyl amino ethyl (meth)acrylate. The invention also provides a method of separating alcohols and esters. In a further form of the invention a process of preparing esters by a transesterification process is provided in which the transesterification catalyst is homogenous.

23 Claims, 1 Drawing Sheet

U.S. PATENT DOCUMENTS

| | | | |
|---|---|---|---|
| 7,767,769 B2 * | 8/2010 | Glos | 526/74 |
| 2002/0123643 A1 | 9/2002 | Paul | |
| 2003/0060587 A1 | 3/2003 | Roos et al. | |
| 2003/0191264 A1 | 10/2003 | Crass et al. | |
| 2006/0211880 A1 | 9/2006 | Ackerman et al. | |

FOREIGN PATENT DOCUMENTS

| | | |
|---|---|---|
| EP | 0118639 | 9/1984 |
| GB | 1572438 | 7/1980 |
| JP | 1299263 | 12/1989 |
| JP | 7-238058 | 9/1995 |
| WO | 8909762 | 10/1989 |
| WO | 0018720 | 4/2000 |
| WO | 02096959 | 12/2002 |
| WO | 2004063140 | 7/2004 |

OTHER PUBLICATIONS

Machine Translation JP07-238058 of Japan 7-238058.
R.C. Poller et al.; Journal of Organometallic Chemistry, 173(1979) C7-C8.
Chemical Abstract—AN 2006:99993 of JP 2006-028066.
English language abstract of EP 0090308 printed from the esp@cenet website on Apr. 24, 2008.
M. Schiller et al.; J. Chem. Eng. Data 1992, vol. 37, pp. 503-508.
Patent abstracts of Japan of JP 1299263.

* cited by examiner

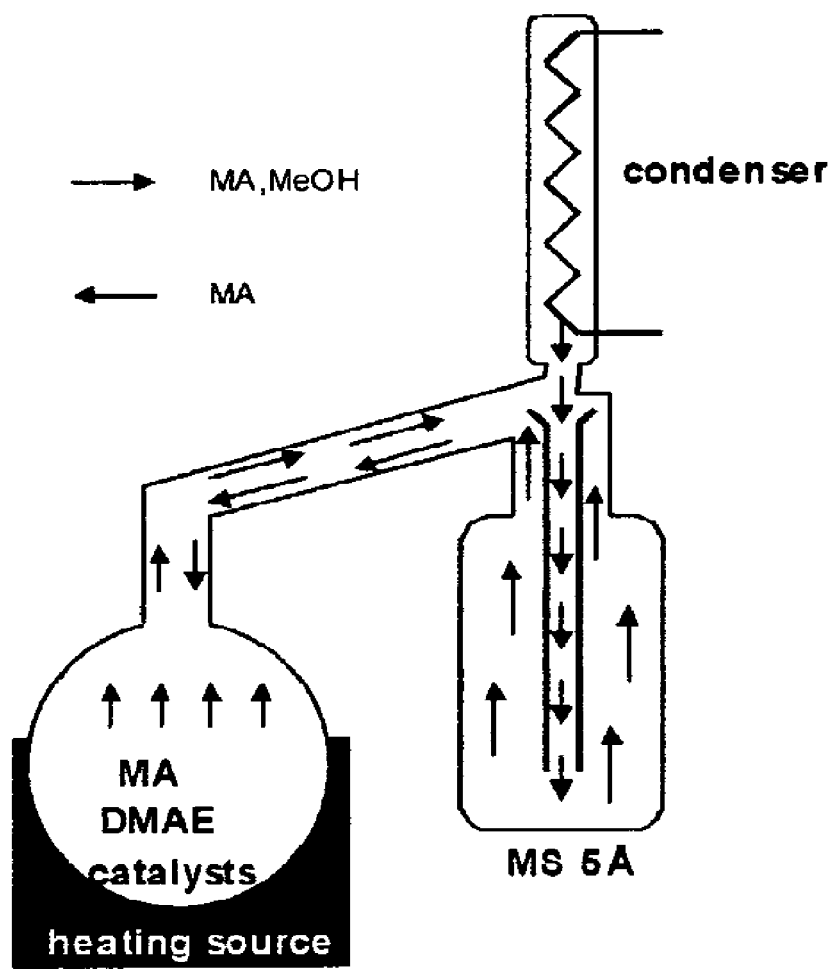

MANUFACTURE OF ESTERS

The present invention relates to a process for the synthesis of esters, especially ethylenically unsaturated esters. The process involves a novel transesterification reaction of an alcohol and ester in the presence of a transesterification catalyst. The invention also relates to a new process of separating an ester and an alcohol.

The production of esters is important for a variety of industrial processes. Ethylenically unsaturated esters can for instance be polymerised to make polymers for a variety of applications. For instance 2-ethyl hexyl acrylate can be copolymerised with styrene to make pressure sensitive adhesives. Acrylate esters of long chain alcohols can be used in the formation of surface active materials and coatings for various substrates. A particularly important class of acrylates include amino alkyl acrylates that can be rendered ionic by forming the acid additions salts or by quaternisation. Suitable amino alkyl acrylates include dimethyl amino ethyl acrylate and dimethyl amino ethyl methacrylate. Corresponding ionic acrylates and methacrylates can be made by the addition of a mineral acid, such as hydrochloric acid or alternatively by quaternisation employing for instance methyl chloride. Particularly preferred ionic acrylates include acryloyl ethyl trimethyl ammonium chloride and meth acryloyl ethyl trimethyl ammonium chloride. Both of these esters can be copolymerised with acrylamide to form high molecular weight polymers suitable as flocculants in the separation of solid and liquids in industrial processes, for instance in the clarification of waste water or in papermaking.

It is known to produce esters by the transesterification of an ester, which may for instance be a lower alkyl ester, with an alcohol, carrying the desired group to be esterified, resulting in the desired ester and an alcohol byproduct. In this type of process it is generally necessary to remove the byproduct alcohol from the reaction medium in order to induce the equilibrium to be in favour of the product formation and thereby driving the reaction forward. The byproduct alcohol (IV) has a tendency to form azeotropes with the starting material ester compound (II). Therefore, in removing the byproduct alcohol (IV), the starting ester compound (II) also tends to be removed from the reaction.

In WO 2004/063140 a process is described for the production of alkyl (meth) acrylates, such as iso-butyl methacrylate, by the continuous catalytic transesterification of methyl (meth)acrylates with high boiling alcohols. In this process tetra iso-butyl titanate is used as a catalyst and repeatedly recycling this catalyst in order to reduce costs. The byproduct alcohol is distilled off as an azeotrope with the methyl (meth) acrylates.

Such removal of the starting ester (II) with the byproduct alcohol (IV) tends to impair the efficiency of the reaction in terms of conversion rate, yield and processing time. The use of hydrocarbons of carbon chain length up to 8 in order to assist the removal of the byproduct alcohol is known.

For instance, U.S. Pat. No. 5,763,644 describes the transesterification synthesis of acrylate and alkyl acrylate esters using a polymerisation inhibitor system. The process employs a basic catalyst and is driven by the removal of the byproduct alcohol with either saturated hydrocarbon of between 5 and 8 carbon atoms or as a methyl methacrylate azeotrope with methanol. In practice the saturated hydrocarbon will form an azeotrope with both the methanol and the methyl methacrylate.

JP 01299263 reveals a batch process for the manufacture of dialkyl amino alkyl(meth)acrylate by the reaction of alkyl (meth)acrylate and dialkyl amino alkyl alcohol using at least one tin compound as a transesterification catalyst. In the example dimethyl amino ethyl acrylate is synthesised from methyl acrylate and dimethyl amino ethanol using di n-butyl tin biacetyl acetonate as a transesterification catalyst and n-hexane as an entrainer. Methyl acrylate, methanol and hexane are removed first by distillation. Methyl acrylate and then dimethyl amino ethanol are distilled batch wise through a reflux column. A conversion rate of dimethyl amino ethyl acrylate of 93.5% is reported with a yield of 90.4%.

JP 7238058 (Daicel Chem) describes the manufacture of tetrahydro benzyl (meth)acrylate using an ester interchange reaction with tetrahydro benzyl alcohol and methyl (meth) acrylate. The process is carried at the presence of an entrainer with methanol having an azeotrope in temperature T1 which satisfies the equation T1<T2 where T1 is an azeotropic temperature of methanol with the entrainer and T2 is an azeotropic temperature of methanol with methyl (meth)acrylate. Hydrocarbons such as n-hexane or cyclohexane are proposed as entrainers.

U.S. Pat. No. 3,784,566 (Texaco) refers to the transesterification of methyl methacrylate with a dialkyl amino ethyl ethanol in presence of an esterification catalyst and an entrainer or azeotrope forming agent such as benzene and the resulting azeotrope is removed overhead from the reaction zone.

U.S. Pat. No. 3,887,609 (Deutsche Texaco AG) describes a process for the production of higher alkyl acrylates and methacrylates by transesterification of methyl acrylate or methacrylate alkanols of three or more carbon atoms in the presence of an entraining agent. The entraining agents for methanol can be any of cyclohexane, cyclopentane, hexane, benzene, methylcyclohexane, methylcyclopentane and dimethylcyclopentane Although the use of hydrocarbons such as hexane, may assist the removal of byproduct alcohols such as methanol by the formation of a low boiling point azeotrope, the starting material ester tends to be removed since the hydrocarbon forms azeotropes with both the alcohol and the ester and in addition the alcohol still forms an azeotrope with the starting material ester. It is then necessary to remove the ester from the alcohol. In such processes using hydrocarbons, the azeotropes distilled from the reaction can be separated into two phases, in which a first phase contains hydrocarbon and is rich in starting material ester and other phase is rich in alcohol. This first phase rich in ester can be recycled into the reaction. However, a certain amount of ester may still be lost in this process.

The separation of esters and alcohols is known. GB 1166928 describes one such process for the separation of mixtures of methanol and lower aliphatic esters using an entrainer. The process involves the azeotropic distillation in the presence of at least one saturated $C_4$ to $C_7$ hydrocarbon, preferably between 5 and 7 carbon atoms. The process involves condensing at least part of the vapours evolved from the distillation column and then separating at least part of the condensed distillate by decantation in the cold into two distinct liquid phases. A portion of the methanol rich phase is refluxed to the distillation column and ester and organic substances are withdrawn from the lower part of the distillation column as a mixture with water. The mixture is subjected to decantation in order to separate the constituents, completely removing the water and methanol from the upper, organic layer by distillation and then distilling the residual liquid to separate the ester from the organic substance. However, since the hydrocarbon forms an azeotrope with both the methanol and the ester, even with such an elaborate process it is still difficult to achieve satisfactory separation of the ester.

WO 00/18720 (GEC) describes the transesterification of dialkyl carbonates to produce diaryl carbonate esters by reaction with aromatic alcohols using reactive distillation and an entrainer. The entraining agent is selected from a group of compounds that do not form azeotropes with the dialkyl carbonate or the alkyl alcohol and that boil at a higher temperature than either dialkyl carbonate or the alkyl alcohol. Any suitable transesterification catalyst can be used. The preferred entrainer is the feed alcohol. The by-product alcohol is removed as distillate.

This process teaches methods of manufacture for carbonate esters not carboxylic esters. In the preferred embodiment, it is specific to processes in which the reactant alcohol acts as an entrainer, as alcoholic entrainers would otherwise produce undesirable side reactions.

In view of the difficulty in separating the byproduct alcohol from the starting material ester in the synthesis of esters, alternative processes that avoid the formation of the byproduct alcohol in the reaction have been developed. EP 118639 describes the synthesis of acrylate or methacrylate esters using a metal alcoholate as a reaction intermediate. The reaction intermediate metal alcoholate is generated by the reaction of a lower alkyl metal alcoholate, for instance tetra methoxy titanium, with an alcohol carrying the desired group. The reaction intermediate metal alcoholate is then reacted with a lower alkyl acrylate or methacrylate, for instance methyl methacrylate. An exchange reaction occurs and the desired acrylate or methacrylate ester is produced and the lower alkyl metal alcoholate is generated as a byproduct. Such a process provides efficient production of the desired ester.

It would be desirable to find a more efficient process which allows the synthesis of esters by direct transesterification of a starting ester and starting alcohol and which provides improved conversion to the product. It would also be desirable to find a process in which the byproduct alcohol can be removed by distillation in a substantially pure form, without the additional processing and cost involved in separation of an azeotrope between an entrainer and the by-product alcohol. It would be particularly advantageous to achieve this at the same time as increasing the production rate.

According to the present invention we provide a process in which a compound $R_1COOR_3$ (I) is made by a transesterification reaction of an ester compound $R_1COOR_2$ (II) with an alcohol $R_3OH$ (III) in the presence of a transesterification catalyst, wherein $R_1$ is H or $C_1$ alkyl or $CH_2=CR_4-$; $R_2$ is $C_{1-4}$ alkyl; $R_3$ is selected from the group consisting of alkyl having at least 4 carbon atoms, cycloalkyl having at least 5 carbon atoms, aryl, aralkyl, alkaryl and amino alkyl; and $R_4$ is —H or —$C_{1-4}$ alkyl,
wherein alcohol $R_2OH$ (IV) is formed as a byproduct and in which said byproduct (IV) is removed by distillation in the presence of an entrainer, in which the entrainer is a compound that suppresses the formation of an azeotrope between compound (II) and byproduct (IV).

The process may be carried out by any convenient means. For instance the reaction may take place in a reaction vessel and the by-product alcohol may be removed by distillation in a distillation column. Preferably, however, the reaction should be carried out by reactive distillation. In this type of process the whole transesterification reaction can be carried out in a distillation column.

In a preferred form of the invention, the transesterification reaction is carried out in the presence of the entrainer and by-product alcohol (IV) is substantially the only compound that is removed as distillate from the reaction by distillation. In this way separation of the by-product alcohol can be achieved simultaneously with carrying out the transesterification reaction.

In an alternative form of the invention the by-product alcohol (IV) and the starting material ester compound (II) are removed together by distillation as a distillate mixture. The mixture may for instance be an azeotrope between the alcohol and the ester. The entrainer may then be introduced into the distillate mixture and this suppresses the formation of an azeotrope in the distillate mixture. The by-product alcohol (IV) may then they removed from the ester compound, for instance by further distillation.

The entrainer may be a substance that either increases the volatility of the by-product alcohol (IV) or decreases the volatility of the ester compound (II). Desirably the entrainer is a substance that brings about a separation factor between the ester compound (II) and the by-product alcohol (IV) at infinite dilution of greater than 2.5 when measured at 345 K. The separation factor is a measure of relative volatilities between the alcohol and the ester. The higher the number the more volatile is the alcohol relative to the ester. The separation factor may be defined as $\alpha_{inf}=\gamma_1 \cdot P_1/\gamma_2 \cdot P_2$ where $\alpha_{inf}$ is the separation factor at infinite dilution. $P_1$ is saturated vapour pressure of component 1 (byproduct alcohol (IV)), $P_2$ is saturated vapour pressure of component 2 (ester compound (II)), $\gamma_1$ is the activity coefficient at infinite dilution for component 1. $\gamma_2$ is the activity coefficient at infinite dilution for component 2 The method for measuring activity coefficients and saturated vapour pressures are determined in accordance with the publication, Schiller, M.; Gmehling, J. Measurement of Activity Coefficients at Infinite Dilution Using Gas-Liquid Chromatography. 4. Results for Alkylene Glycol Dialkyl Ethers as Stationary Phases. *J. Chem. Eng. Data,* 1992, Vol. 37, Issue 4, 503-508.

Preferably, the separation factor is greater than 5. There is no maximum separation factor since the higher the number the greater the opportunity for separation of the ester and the alcohol. The separation factor may be as high as 100 but is generally up to 50 and often within the range of between 5 and 20. The separation factor for dibenzyl ether based on the ratio of relative volatilities of methyl acrylate and methanol at infinite dilution is 5.366 at 345 K. Other compounds including diethylene glycol dibutyl ether, diethylene glycol di-n-butyl ether, triethylene glycol dibutyl ether, diethylene glycol diethyl ether and tripropylene glycol dimethyl ether. have separation factors of 4.18, 5.05, 3.68, 3.10 and 2.61 respectively all at 345 K Generally the entrainer should be a liquid with a boiling temperature at least 10° C. higher than the alcohol (IV). The difference in boiling temperature is generally higher than this, for instance at least 20° C. and can be as much as 60 or 70° C. or higher. If an additional azeotrope is introduced by the entrainer it is usually only with the byproduct alcohol and this would most desirably be heterogeneous. This means that ideally the entrainer will not form an azeotrope with any compound. The entrainer could be used if it formed an azeotrope with the byproduct alcohol, provided that azeotrope was heterogeneous. Normally it would be not be suitable for use as an entrainer if it formed an azeotrope with a compound other than the byproduct alcohol. Most desirably no additional azeotropes will be introduced.

Typically the entrainer can be a compound selected from the group consisting of ethers, alkanes of at least 11 carbon atoms, aromatics and chlorinated alkanes.

Useful alkanes for use in the present invention may for instance have between 8 and 20 carbon atoms or higher and include compounds such as, n-dodecane, n-tridecane, n-tetradecane, n-pentadecane, branched alkanes such as 2-methyldecane, and cyclic alkanes such as 1,4-diethyl cyclohexane etc. The aromatics useful in the invention include alkyl substituted benzenes having at least 10 carbon atoms, such as n-butylbenzene, n-pentyl benzene, and halogenated aromatics such as chlorinated or brominated aromatics having greater than seven carbon atoms such as 4-bromotoluene. Chlorinated alkanes include compounds such as 1-chlorooctane and 1,6-dichloro hexane. Preferred entrainers include ethers, especially aromatic and glycol ethers. Particularly preferred amongst these are compounds selected from the group consisting of dibenzyl ether, diethylene glycol dibutyl ether, diethylene glycol di-n-butyl ether, triethylene glycol dibutyl ether, diethylene glycol diethyl ether and tripropylene glycol dimethyl ether.

It is possible to carry out the process of the invention using any conventional transesterification catalyst and typical catalysts are discussed in the prior art, for instance in the documents described above. Suitable transesterification catalysts are generally metal compounds. Preferred catalysts include those compounds selected from the group selected from the group consisting of tin salts, titanium salts, zinc salts, lanthanum salts, samarium salts and neodymium salts. The catalyst may be solid provided that it can be distributed easily throughout the reaction medium. Suitably the catalyst can be particulate and desirably exhibits a relatively high surface area. Effective yields can be achieved with such a heterogenous catalyst system employing solid catalyst.

It is possible to prepare a soluble catalyst by forming a compound based on one or more of the above named metal catalyst compounds with suitable ligands. Preferably the compounds forming the ligands include amino alkanes having at least two amino groups, for instance N,N,N'-trimethylethylenediamine or N,N,N',N",N"-pentamethyldiethylenetriamine.

We have found a particularly effective catalyst for use in the present invention include metal compounds selected from the group consisting of dibutyl tin dichloride, dibutyl tin oxide, dibutyl tin diacetate, dibutyl tin bromide, tin tetrachloride, tin triflate, tin bis acetoacetate, tetraisopropyl titanate and tetra dimethyl amino ethyl titanate.

In a further aspect of the present invention we have found that improved conversion to the ester product and processing time can be achieved when the catalyst is homogenous with the reaction medium. The catalyst may be either soluble in the reaction medium and therefore dissolved in it or it may be miscible with the reaction medium. Preferably the catalyst is liquid. A particularly preferred transesterification catalyst is selected from the group consisting of dibutyl tin diacetate, dibutyl tin diacrylate and metal salts rendered soluble by ligands selected from trimethyl ethylenediamine or pentamethyldiethylene triamine.

It may also be desirable to include a polymerisation inhibitor in the reaction medium when at least one of the reactants and/or products is/are ethylenically unsaturated compounds in order to prevent undesirable polymerisation during the reaction. Any conventional polymerisation inhibitor may be suitable for this purpose. Particularly suitable polymerisation inhibitors include phenothiazine. In addition to preventing unwanted polymerisation it is often necessary to carry the reaction out in the absence of air and thus would be carried out in an essentially oxygen free medium.

In a preferred form of the process, the transesterification reaction is carried out in a column. The entrainer and catalyst are fed into the upper end of the column, preferably as close to the top as is feasible. The entrainer and catalyst may be combined into a feed mixture or alternatively fed into the upper end of the column separately. The entrainer and catalyst can then move down the column so that they are distributed throughout the column. The starting material ester compound (II) and starting material alcohol (III) are fed into the distillation column. The alcohol (III) and ester (II) are fed into the distillation column at any suitable point. Generally though, it will often be desirable to feed the alcohol (III) around the middle to upper region of the distillation column. This can for instance be on to a distillation tray between one half and one quarter from the top of the column, for instance around one-third from the top. Typically the ester should be fed in towards a lower end of the distillation column, especially when the ester exhibits high volatility and the ester will hence tend to move up through the column. Typically the ester (II) should be fed into the column on to a distillation tray in the bottom half of the column, preferably around two-thirds or below from the top. The product ester compound (I) and the byproduct alcohol (IV) are formed in the distillation column from which the byproduct alcohol (IV) is evaporated and removed as distillate from the column. The distillation column should be maintained under reflux during the reaction and may also be under reduced or positive pressure.

Typically a mixture of catalyst and entrainer can be fed into the upper end of the distillation column at a rate of between 5 and 80 (e.g. between 5 and 40) kilograms per hour of catalyst and between 150 and 1500 (e.g. between 150 and 700) kilograms per hour of the entrainer. Although it is not always necessary to maintain a reaction under reduced pressure typically the distillation column would be under reflux and operated at a pressure between 0.4 and 3.0 bar. The refluxing temperature of the reaction medium will depend upon the constituents and the pressure. The alcohol (III) is ideally fed on to a distillation tray approximately one-third or higher from the top of the distillation column. A suitable feed rate of alcohol (III) would be between 75 and 125 kilograms per hour, for instance around 100 kilograms per hour. The ester (II) is preferably fed into the distillation column approximately two-thirds or below from the top of the distillation column. A suitable feed rate of ester (II) would be for instance between 100 and 250 or 350 kilograms per hour. Suitably the process should be operated with sufficient residence time in the distillation column to achieve conversion of the ester (II) and alcohol (III) to ester product (I) should be desirably in excess of 95% by weight. The residence time will usually be at least two minutes, often at least ten minutes and may be as much as three or four hours or more. Typically the residence time may be between 5 minutes and one hour. This could be between 15 minutes and one-hour. An alternative range in some cases may be between 8 and 45 minutes, for instance between 30 and 45 minutes.

We have found that the entrainer can reduce the volatility of starting material ester (II) without a corresponding effect on the byproduct alcohol (IV) or alternatively increases the volatility of the byproduct alcohol (IV) without having a corresponding effect on the starting material ester (II) or in a further alternative form increases the volatility of the byproduct alcohol (IV) and reduces the volatility of the starting material ester (II). Typically according to the present invention the distillate from the distillation column is byproduct alcohol (IV) with no or a very low concentration of starting material ester (II). In general the concentration of ester (II) will be less than 3% by weight of total distillate and typically may be in the range of between 0.5 and 3%.

In a more preferred form of the invention it is desirable that the ester (II) is used in stoichiometric excess. This ensures that substantially all the starting material alcohol (III) is used up in the reaction. However, in this more preferred form it is desirable to recover the least a portion of the ester (II) and preferably also alcohol (III). Thus the product ester (I), unreacted ester compound (II), and when necessary any unreacted alcohol (III), entrainer and catalyst can be transferred to a second distillation column or any other convenient means of separation. In this second distillation column unreacted ester (II) and where present alcohol (III) is evaporated and removed. The unreacted ester (II) and any unreacted alcohol (III) may then be recovered and used again in the transesterification process. For instance the recovered ester (II) may be fed back into the first distillation column in which the transesterification reaction takes place. It can for instance be combined with the ester (II) feed to the distillation column.

In general it will often be desirable to recover the entrainer and catalyst for reuse. In any event the product ester (I) will need to be separated from the catalyst and the entrainer. A suitable separation process may be employed but generally this is achieved by distillation. In a further preferred process the product ester (I), entrainer and catalyst are transferred from the second distillation column to a third distillation column and in which product ester (I) is separated from the entrainer and catalyst. It is generally achieved by evaporating the product ester (I) and removing it from the top of the column and recovering it and then recovering the entrainer and catalyst from the bottom of the column. The entrainer and catalyst desirably can then be returned to the first distillation column in which the transesterification reaction takes place.

In an even more preferred alternative the product ester (I), unreacted ester compound (II) and unreacted alcohol (III) from the reactive distillation column are first separated from the entrainer and catalyst by evaporation, which may be at reduced pressure. The catalyst and entrainer may be recycled to the first distillation column. The product ester (I) can then be separated from unreacted ester compound (II) and unreacted alcohol (III) for instance in a second distillation column. Recovered ester compound (II) and alcohol (III) can then be recycled to the first distillation column.

The transesterification reaction may be as a batch process but preferably it is a continuous process. Thus preferably reaction is continuous in which the components starting material ester (II) and starting material alcohol (III) are continually fed into the reaction, for instance distillation column, and byproduct alcohol (IV) is continuously removed and in which ester compound (II), entrainer and catalyst are continuously fed back into the reaction.

The process of the present invention may be used to prepare any suitable ester from a starting material ester and alcohol. Preferably the product ester is a compound in which $R_3$ is an amino alkyl group, more preferably an alkyl amino alkyl group, in particular dimethyl amino ethyl. Thus particularly preferred products according to the present invention are dimethyl amino ethyl acrylate and dimethyl amino ethyl methacrylate. Thus in both cases the starting material alcohol (III) will be dimethyl amino ethanol and the starting material ester (II) will be a suitable acrylate or methacrylate ester, for instance methyl acrylate or methyl methacrylate.

In another preferred form $R_2$ on the starting material ester (II) and the byproduct alcohol (IV) is a lower alkyl group, for instance $C_{1-4}$ alkyl, in particular a methyl group. Thus preferably the starting material ester (II) will be a methyl ester of a suitable acid, for instance methyl acrylate or methyl methacrylate and the byproduct alcohol will be methanol.

In an alternative form of the invention the reaction is non continuous. In this form byproduct alcohol (IV) can be removed and the ester compound (II), entrainer and catalyst can be batch distilled and then fed back into the reaction. The most preferred form of operating the invention concerns the continuous manufacture of dimethyl amino methyl acrylate as product ester (I). The process will preferably be carried out in a reactive distillation column by the transesterification of dimethyl amino ethanol as starting alcohol (III) with methyl acrylate (II) as the starting material ester and using a homogenous catalyst. The catalyst is most preferably dibutyl tin diacetate. The preferred entrainer is dibenzyl ether the use of which results in the separation of the azeotrope that forms between methyl acrylate and methanol and achieves a high conversion of the reactants. The reaction is preferably carried out in the presence of polymerisation inhibitor, especially phenothiazine. Preferably the reaction is carried out in the absence of air.

In a particularly preferred form of this process a feed containing the mixture of the catalyst at between 5 and 40 kg per hour, often between 5 and 30 kg per hour, especially from 25 to 28 kg per hour and the entrainer between 300 and 1200 kg per hour. Typically this may be between 300 and 600 kg per hour such as 550 kg per hour but often it is preferred that this is much higher, for instance 700 to 1200 kg per hour especially 1150 kg per hour is fed into the upper end or top of the distillation column which is refluxed and operating at between 0.6 and 2.0 bar. Between 75 and 125 kilograms per hour, especially around 100 kilograms per hour of dimethyl amino ethanol (III) is fed on to a distillation tray approximately between one half and three-quarters, especially around one-third, from the top of the distillation column and between 120 and 300 kilograms per hour. Typically this may be between 120 and 200 kg per hour such as 160 kg per hour but often it is preferred that this is higher, for instance 120 to 300 kg per hour especially around 250 kilograms per hour. Methyl acrylate (II) is fed into the distillation column between half and the bottom, especially around nine-tenths, from the top of the distillation column.

The column is operated with sufficient residence time of up to 150 minutes, especially between 8 and 90 minutes, for instance between 30 and 90 minutes, in the column to achieve conversions of the reactants to the product dimethyl amino ethyl acrylate above 99%. The entrainer has been found to improve the separation of the methanol while promoting high reaction rates and allowing a separation by distillation of methyl acrylate and methanol and in which the distillate from the top of the distillation column is methanol with a low concentration of methyl acrylate for instance below 1.5% by weight, especially 1.1% or lower.

In a further aspect of the invention we provide a process of removing an alcohol $R_2OH$ (IV) by distillation from a mixture of an ester compound $R_1COOR_2$ (II) and said alcohol (IV) by introducing an entrainer into said mixture and subjecting the mixture to the distillation conditions, wherein $R_1$ is H or $C_{1-4}$ alkyl or $CH_2$=$CR_4$—; $R_2$ is $C_{1-4}$ alkyl; $R_2$ is $C_{1-4}$ alkyl; $R_4$ is —H or —$C_{1-4}$ alkyl and the entrainer is selected from the group consisting of ethers, alkanes of at least eleven carbon atoms, aromatics and chlorinated alkanes.

The entrainer may be a substance that either increases the volatility of byproduct alcohol (IV) or decreases the volatility of the ester compound (II)

Desirably the entrainer is a substance that brings about separation factor between the ester compound (II) and the byproduct alcohol (IV) at infinite dilution of greater than 2.5 or less than (0.4). The separation factor is a measure of relative volatilities between the alcohol and the ester. The higher the number the more volatile is the alcohol. Thus in this aspect of the invention it is desirable to provide a compound that either increases the volatility of the alcohol relative to the ester so that the alcohol can be distilled off alternatively a compound that the decreases the volatility of the alcohol relative to the ester so that the ester can be distilled off.

The process enables the convenient separation of alcohols and esters in a suitable distillation step. The entrainer may be any of the compounds identified in regard to the first aspect of this invention. Preferably the entrainer is a compound selected from the group consisting of dibenzyl ether, diethylene glycol dibutyl ether, diethylene glycol di-n-butyl ether, triethylene glycol dibutyl ether, diethylene glycol diethyl ether and tripropylene glycol dimethyl ether.

In this second aspect of the invention the separation of the ester and the alcohol may be a of the transesterification process carried out in regard to the first aspect of the invention. Thus either the separation takes place in the distillation column where the transesterification occurs or alternatively the ester and alcohol are removed from the transesterification distillation column and transferred to a further distillation column in which the ester and the alcohol can then be separated by use of the entrainer. Most preferably the entrainer is dibenzyl ether and the ester and alcohol are methyl acrylate and methanol respectively.

In a further aspect of the invention we provide a process in which a compound $R_1COOR_3$ (I) is made by a transesterification reaction of an ester compound $R_1COOR_2$ (II) with an alcohol $R_3OH$ (III) in the presence of a transesterification catalyst in a reaction medium, wherein $R_1$ is H or $C_{1-4}$ alkyl or $CH_2=CR_4-$; $R_2$ is $C_{1-4}$ alkyl; $R_3$ is selected from the group consisting of alkyl having at least 4 carbon atoms, cycloalkyl having at least 5 carbon atoms, aryl, aralkyl, alkaryl and amino alkyl; and $R_4$ is —H or —$C_{1-4}$ alkyl, and alcohol $R_2OH$ (IV) is formed as a byproduct in which the catalyst is homogenous with the reaction medium.

In this aspect of the invention it is desirable that the catalyst is dissolved in the reaction medium or is miscible with the reaction medium. Preferably the transesterification catalyst is a liquid catalyst. More preferably the catalyst is liquid and is either dibutyl tin diacetate or dibutyl tin diacrylate. Alternatively the catalyst may be a metal salt that has been rendered soluble by the use of ligands as indicated in regard to the first aspect of the invention. Suitably the catalyst may be a metal salt having ligands containing amino alkanes having at least two amino groups, for instance N,N,N'-trimethylethylenediamine or N,N,N',N'',N''-pentamethyldiethylenetriamine.

The following examples are an illustration of the invention without in any way intending to limit the full scope of the invention.

EXAMPLES

Preparation of Dimethyl Amino Ethyl Acrylate (DMAEA)

Example A

A 1000 ml borosilicate stirred tank reactor (CSTR) is charged with 178 g DMAE (dimethyl amino ethanol) and 198.2 DBE (dibenzyl ether). To ensure an inert atmosphere is present throughout the test work, a small nitrogen purge is passed through into the flask at all times.

After heating to the desired operating temperature of 110° C., a spot sample (t=0 min) is taken and immediately 35 g dibutyl tin diacetate catalyst is added via a cannula. Methyl acrylate (MA) feed, at 344 g/h, is then started. The methyl acrylate is pumped as a liquid via a stainless steel cannula into the CSTR below the level of the process fluids, vaporizing in the cannula and entering the process liquid as a vapour. Light materials formed during the reaction (methanol and some carry over of DMAE and DMAEA) were collected via a condenser into a flask. Bulk overheads and 'spot' pot contents samples are taken at set intervals throughout the reaction. All samples are quenched to room temperature and analysed by GC. The feeds are stopped after 120 min. The conversion of DMAE at this time is 94.8%.

Example B

A continuous feed containing a mixture of catalyst 25 kg/h and entrainer 550 kg/h is fed to the top of a distillation column which is refluxed and operating at 1.4-1.6 bar. 100 kg/h of alcohol (III) is fed onto a distillation tray approximately ⅓ of way from the top distillation column and 160 kg/h acrylate (II) approximately 9/10 of way from the top distillation column. The column is operated with a residence time of 40 min in the column to achieve conversions of alcohol (III) to product (I) in excess of 99%. The entrainer reduces the volatility of (II) without a corresponding effect on (IV) which has the dual purpose of promoting high reaction rates and allowing a separation by distillation of (II) and (IV). The distillate from the top of the distillation column is methanol with a low concentration of MA (1.1%). The bottom stream from the reactive distillation column is further distilled to separate the constituents. Excess MA and small quantities of DMAE are first distilled and recycled to the reactive distillation column. Product DMAEA is separated by distillation from entrainer and catalyst which are also recycled to the reactive distillation column.

Example C

A continuous feed containing a mixture of catalyst 25 kg/h and entrainer 1000 kg/h is fed to the top of a distillation column which is refluxed and operating at atmospheric pressure. 100 kg/h of alcohol (III) is fed onto a distillation tray approximately ⅓ of way from the top distillation column and 250 kg/h acrylate (II) approximately 9/10 of way from the top distillation column. The column is operated with a residence time of 9 min in the column to achieve conversions of (III) to product (I) in excess of 99%. The entrainer reduces the volatility of (II) without a corresponding effect on (IV) which has the dual purpose of promoting high reaction rates and allowing a separation by distillation of (II) and (IV). The distillate from the top of the distillation column is methanol with a low concentration of MA (1.1%). The bottom stream from the reactive distillation column is further distilled to separate the constituents. Excess MA and small quantities of DMAE are first distilled and recycled to the reactive distillation column. Product DMAEA is separated by distillation from entrainer and catalyst which are also recycled to the reactive distillation column.

Example D

A continuous feed containing a mixture of catalyst 25 kg/h and entrainer 1000 kg/h is fed to the top of a distillation column which is refluxed and operating at atmospheric pressure. 100 kg/h of alcohol (III) is fed onto a distillation tray approximately ⅓ of way from the top distillation column and 250 kg/h acrylate (II) approximately 9/10 of way from the top distillation column. The column is operated with a residence time of 9 min in the column to achieve conversions of (III) to product (I) in excess of 99%. The entrainer reduces the volatility of (II) without a corresponding effect on (IV) which has the dual purpose of promoting high reaction rates and allowing a separation by distillation of (II) and (IV). The distillate from the top of the distillation column is methanol with a low concentration of MA (1.1%). The bottom stream from the reactive distillation column is further distilled to separate the constituents. Excess MA, product DMAEA and small quantities of DMAE are first evaporated at reduced pressure from entrainer and catalyst which are recycled to the reactive distillation column. Product DMAEA is separated by distillation from excess MA and small quantities of DMAE which are also recycled to the reactive distillation column Example E 300 kg/h of dibenzyl ether is fed to the top of a continuously operating distillation column and 100 kg/h of an azeotropic mixture of methanol and methyl acrylate comprising 44% w/w 56% methanol is fed to the centre of this column which operates at atmospheric pressure. A stream from the top of the column contains the majority (99%) of methanol fed to the column and at high concentrations 98% The majority 97% of the methyl acrylate is in the bottom stream from the column and can be evaporated from dibenzyl ether.

Example F

Reaction profiles are determined using a modified Dean-Stark like equipment (see FIG. 1). Using this set-up an efficient removal of methanol on a laboratory scale is achieved allowing complete conversion. In the beginning 10.0 g (0.11 mol) DMAE and 20.0 g (0.23 mol) MA is placed in the reaction flask at room temperature. After the catalyst addition the flask is put in a hot oil bath (110° C.). The high temperature is chosen to ensure efficient distillation of the MA/methanol azeotrope. Methanol is removed by the molecular sieve and excess MA is returned to the flask. Samples are taken every 15 minutes for the first hour and analyzed by GC. After two hours the reactions were stopped.

Table 1 lists the yields and selectivities that were achieved for the catalysts listed.

TABLE 1

|  | Yield after 2 hrs | Selectivity |
| --- | --- | --- |
| Ti(DMAE)$_4$ | 94% | 99% |
| La(OTf)$_3$ | 93% | 95% |
| La(ClO$_4$)$_3$ | 85% | 97% |
| La(NO$_3$)$_3$ | 48% | 94% |
| La(acac)$_3$ | 40% | 86% |
| Nd(OTf)$_3$ | 89% | 98% |
| Nd(OAc)$_3$ | 88% | 96% |
| Nd(NO$_3$)$_3$ | 68% | 97% |
| Sm(OTf)$_3$ | 97% | 98% |
| ZnCl$_2$ | 62% | 94% |
| Zn(NO$_3$)$_2$ | 72% | 96% |

Preparation of Dimethyl Amino Ethyl Methacrylate (DMAEMA)

Example G

A 1000 ml borosilicate stirred tank reactor (CSTR) is charged with 106.8 g DMAE (dimethyl amino ethanol) and 119.1 DBE (dibenzyl ether). To ensure an inert atmosphere is present throughout the test work, a small nitrogen purge is passed through into the flask at all times.

After heating to the desired operating temperature of 115° C., a spot sample (t=0 min) is taken and immediately 5.34 g dibutyl tin diacetate catalyst is added via a cannula. Methyl methacrylate (MMA) feed, at 240 g/h, is then started. The methyl methacrylate is pumped as a liquid via a stainless steel cannula into the CSTR below the level of the process fluids, vaporizing in the cannula and entering the process liquid as a vapour. Light materials formed during the reaction (methanol and some carry over of DMAE and DMAEMA) were collected via a condenser into a flask. Bulk overheads and 'spot' pot contents samples are taken at set intervals throughout the reaction. All samples are quenched to room temperature and analysed by GC. The feeds are stopped after 120 min. The conversion of DMAE at this time is 79.8%.

The invention claimed is:

1. A process of making a compound $R_1COOR_3$ (I) comprising:
   (i) reacting an ester compound $R_1COOR_2$ (II) with an alcohol $R_3OH$ (III) in the presence of a transesterification catalyst in a transesterification reaction,
   wherein $R_1$ is H or $C_{1-4}$ alkyl or $CH_2$=$CR_4$—,
   $R_2$ is $C_{1-4}$ alkyl,
   $R_3$ is selected from the group consisting of alkyl having at least 4 carbon atoms, cycloalkyl having at least 5 carbon atoms, aryl, aralkyl, alkaryl and amino alkyl, and
   $R_4$ is —H or —$C_{1-4}$ alkyl;
   (ii) forming alcohol $R_2OH$ (IV) as a byproduct; and
   (iii) removing said byproduct (IV) by distillation in the presence of an entrainer,
   wherein the entrainer is a compound that suppresses the formation of an azeotrope between compound (II) and byproduct (IV),
   wherein the entrainer is selected from the group consisting of ethers, alkanes of at least eleven carbon atoms, and chlorinated alkanes,
   wherein the entrainer brings about a separation factor between the ester compound (II) and the byproduct (IV) at infinite dilution of greater than 2.5 when measured at 345 K,
   wherein the separation factor is a measure of the relative volatilities between the byproduct (IV) and the ester compound (II), and
   wherein the transesterification reaction is carried out in the presence of the entrainer and byproduct (IV) is substantially the only compound removed from the reaction by distillation.

2. A process according to claim 1 in which the reaction is carried out by reactive distillation.

3. A process according to claim 1 in which byproduct (IV) and ester compound (II) are removed from the reaction by distillation as a distillate mixture and then an entrainer is introduced into the distillate mixture and byproduct (IV) is removed from said compound (II) in a separate distillation step.

4. A process according to claim 1 in which the entrainer is a compound selected from the group consisting of dibenzyl ether, diethylene glycol dibutyl ether, diethylene glycol di-n-butyl ether, triethylene glycol dibutyl ether, diethylene glycol diethyl ether and tripropylene glycol dimethyl ether.

5. A process according to claim 1 in which the transesterification catalyst is a metal compound is selected from the group consisting of tin salts, titanium salts, zinc salts, lanthanum salts, samarium salts and neodymium salts.

6. A process according to claim 5 in which the transesterification catalyst is a metal salt that is made soluble by ligands selected from trimethyl ethylenediamine or pentamethyldiethylene triamine.

7. A process according to claim 1 in which the transesterification catalyst is a metal compound selected from the group consisting of dibutyl tin dichloride, dibutyl tin oxide, dibutyl tin diacetate, dibutyl tin bromide, tin tetrachloride, tin triflate, tin bis acetoacetate, tetraisopropyl titanate and tetra dimethyl amino ethyl titanate.

8. A process according to claim 1 in which the transesterification catalyst is homogeneous with the reaction medium.

9. A process according to claim 8 in which the transesterification catalyst is selected from the group consisting of dibutyl tin diacetate, dibutyl tin diacrylate and metal salts rendered soluble by ligands selected from trimethyl ethylenediamine or pentamethyldiethylene triamine.

10. A process according to claim 1 in which the entrainer and catalyst are fed into the upper part or top of a first distillation column which is maintained under reflux and optionally under reduced pressure, and in which ester compound (II) and alcohol (III) are fed into the distillation column, wherein compound (I) and byproduct (IV) are formed and byproduct (IV) is evaporated and removed from the top of the first distillation column.

11. A process according to claim 10 in which the ester component (II) is used in stoichiometric excess and in which compound (I), unreacted ester compound (II), entrainer and catalyst are transferred to a second distillation column and in which unreacted ester compound (II) is evaporated and removed from the second distillation column.

12. A process according to claim 11 in which compound (I), entrainer and catalyst are transferred to a third distillation column and in which compound (I) is separated from the entrainer and catalyst and collected.

13. A process according to claim 10 in which the ester component (II) is used in stoichiometric excess and in which compound (I), unreacted ester compound (II), entrainer and catalyst are transferred to an evaporator and in which unreacted ester compound (II) and compound (I), are evaporated and removed from the evaporator.

14. A process according to claim 13 in which compound (I) and ester component (II), are transferred to a second distillation column and in which compound (I) is separated from ester component (II) and collected.

15. A process according to claim 1 in which the reaction is continuous in which byproduct (IV) is continuously removed and in which ester compound (II), entrainer and catalyst are continuously fed back into the reaction.

16. A process according to claim 1 in which $R_3$ is an amino alkyl group.

17. A process according to claim 1 in which $R_2$ is a methyl group.

18. A process according to claim 1 in which the reaction is non continuous in which byproduct (IV) is removed and in which ester compound (II), entrainer and catalyst are batch distilled then fed back into the reaction.

19. A process of removing a byproduct alcohol $R_2OH$ (IV) comprising:
   (i) reacting an ester compound $R_1COOR_2$ (II) with an alcohol $R_3OH$ (III) in the presence of a transesterification catalyst in a transesterification reaction,
   wherein $R_1$ is H or $C_{1-4}$ alkyl or $CH_2$=$CR_4$—,
   $R_2$ is $C_{1-4}$ alkyl,
   $R_3$ is selected from the group consisting of alkyl having at least 4 carbon atoms, cycloalkyl having at least 5 carbon atoms, aryl, aralkyl, alkaryl and amino alkyl, and
   $R_4$ is —H or —$C_{1-4}$ alkyl;
   (ii) forming alcohol $R_2OH$ (IV) as the byproduct; and
   (iii) removing said byproduct (IV) by distillation in the presence of an entrainer, wherein the entrainer is a compound that suppresses the formation of an azeotrope between compound (II) and byproduct (IV),
   wherein the entrainer is selected from the group consisting of ethers, alkanes of at least eleven carbon atoms, and chlorinated alkanes,
   wherein the entrainer brings about a separation factor between the ester compound (II) and the byproduct (IV) at infinite dilution of greater than 2.5 when measured at 345 K,
   wherein the separation factor is a measure of the relative volatilities between the byproduct (IV) and the ester compound (II), and
   wherein the transesterification reaction is carried out in the presence of the entrainer and byproduct (IV) is substantially the only compound removed from the reaction by distillation.

20. A process according to claim 1 in which the entrainer is dibenzyl ether.

21. A process of making a compound $R_1COOR_3$ (I) comprising:
   (i) reacting an ester compound $R_1COOR_2$ (II) with an alcohol $R_3OH$ (III) in the presence of a transesterification catalyst in a reaction medium by a transesterification reaction,
   wherein $R_1$ is H or $C_{1-4}$ alkyl or $CH_2$=$CR_4$—,
   $R_2$ is $C_{1-4}$ alkyl,
   $R_3$ is selected from the group consisting of alkyl having at least 4 carbon atoms, cycloalkyl having at least 5 carbon atoms, aryl, aralkyl, alkaryl and amino alkyl, and
   $R_4$ is —H or —$C_{1-4}$ alkyl;
   (ii) forming alcohol $R_2OH$ (IV) as a byproduct in which the catalyst is homogenous with the reaction medium;
   (iii) removing said byproduct (IV) by distillation in the presence of an entrainer,
   wherein the entrainer is a compound that suppresses the formation of an azeotrope between compound (II) and byproduct (IV),
   wherein the entrainer is selected from the group consisting of ethers, alkanes of at least eleven carbon atoms, and chlorinated alkanes,
   wherein the entrainer brings about a separation factor between the ester compound (II) and the byproduct (IV) at infinite dilution of greater than 2.5 when measured at 345 K,
   wherein the separation factor is a measure of the relative volatilities between the byproduct (IV) and the ester compound (II), and
   wherein the transesterification reaction is carried out in the presence of the entrainer and byproduct (IV) is substantially the only compound removed from the reaction by distillation.

22. A process according to claim 21 in which the transesterification catalyst is selected from the group consisting of dibutyl tin diacetate, dibutyl tin diacrylate and metal salts rendered soluble by ligands selected from trimethyl ethylenediamine or pentamethyldiethylene triamine.

23. A process according to claim 1, wherein the separation factor is up to 50.

* * * * *